United States Patent [19]

Takamizawa et al.

[11] 4,136,325
[45] Jan. 23, 1979

[54] ULTRASONIC WAVE TRANSMITTING AND RECEIVING APPARATUS

[75] Inventors: Kinya Takamizawa; Kazuhiro Iinuma, both of Yokohama, Japan

[73] Assignee: Tokyo Shibaura Electric Co., Ltd., Kawasaki, Japan

[21] Appl. No.: 699,227

[22] Filed: Jun. 23, 1976

[30] Foreign Application Priority Data

Jun. 24, 1975 [JP] Japan .................. 50-78067

[51] Int. Cl.$^2$ ............. G01S 9/66; G01S 7/62
[52] U.S. Cl. .................. 340/1 R; 73/626; 340/3 C; 340/5 MP
[58] Field of Search .......... 340/1 R, 3 C, 6.5

[56] References Cited

U.S. PATENT DOCUMENTS

| | | | |
|---|---|---|---|
| 3,370,267 | 2/1968 | Barry | 340/6.5 |
| 3,790,925 | 2/1974 | Ahrens | 340/3 R |
| 3,914,730 | 10/1975 | Jones et al. | 340/3 C |
| 3,919,683 | 11/1975 | Itamura et al. | 340/1 R |
| 3,921,122 | 11/1975 | Chirstoff | 340/3 C |
| 4,024,490 | 5/1977 | Wood et al. | 340/3 R |

Primary Examiner—Richard A. Farley
Attorney, Agent, or Firm—Oblon, Fisher, Spivak, McClelland & Maier

[57] ABSTRACT

An ultrasonic wave transmitting and receiving apparatus comprises a plurality of electrical-acoustic converting elements arranged in the same plane; a clock pulse generator; a plurality of first switching circuits coupled between the clock pulse generator and each of the electrical-acoustic converting elements; a data signal receiving circuit; a plurality of second switching circuits coupled between the data signal receiving circuit and each of the electrical-acoustic converting elements; a first control circuit adapted to control the first switching circuit so as to radiate a beam of ultrasonic wave from the electrical-acoustic converring element into a to-be-measured subject by sequentially supplying the clock pulse of the clock pulse generator; and to control the second switching circuit so as to sequentially supply to the data signal receiving circuit an electric signal generated from the electrical-acoustic converring element which receives a beam of ultrasonic wave reflected from the subject; three memories coupled to the data signal receiving circuit; a second control circuit adapted to control the memories so as to sequentially write at a predetermined rate data signals from the data signal receiving circuit into the memories and, when the data signal is being written into one of the memories, read data at a rate higher than the predetermined rate from the remaining memories; and an addition circuit adapted to add together the readout data signal from the memories so as to deliver an output.

11 Claims, 46 Drawing Figures

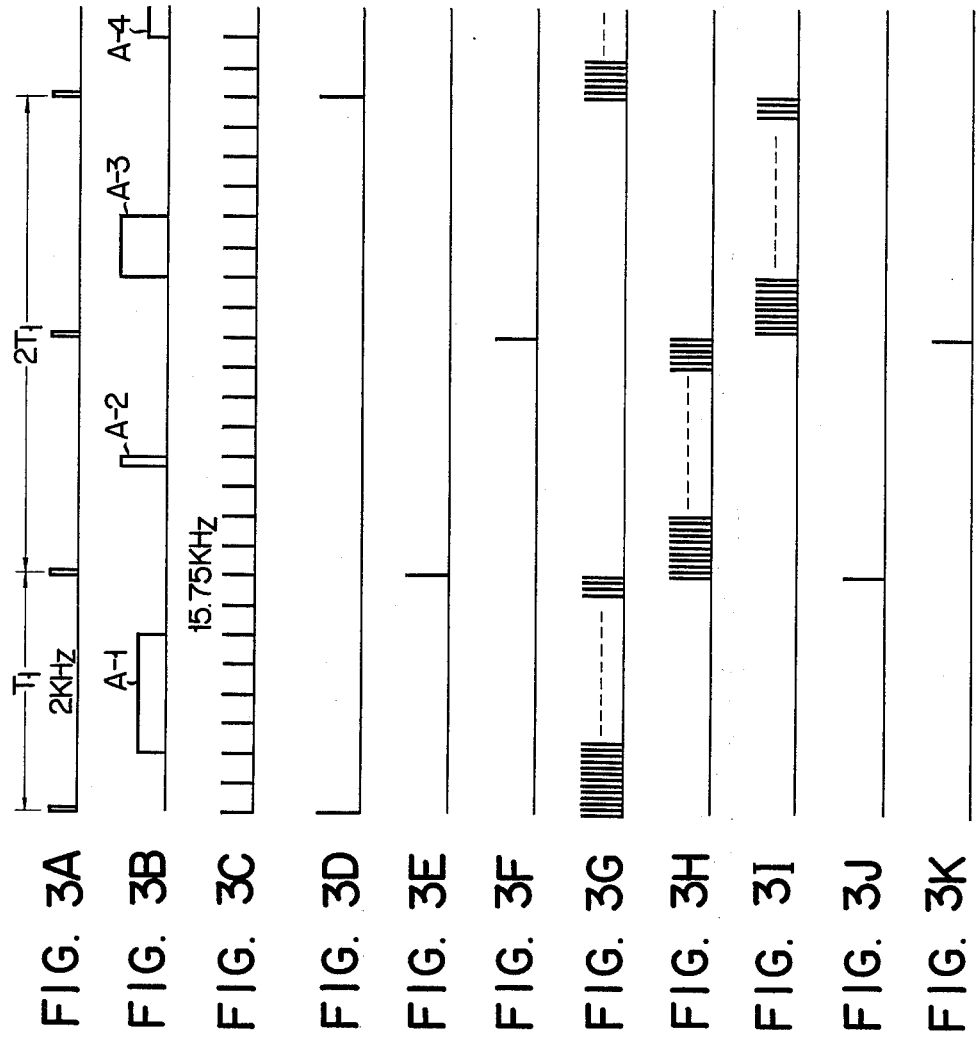

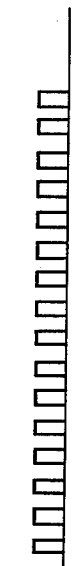
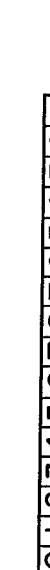
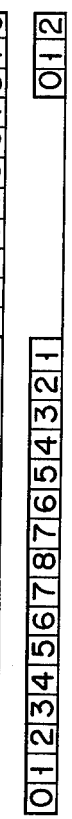
FIG. 3L
FIG. 3M
FIG. 3N
FIG. 3P
FIG. 3Q
FIG. 3R
FIG. 3S
FIG. 3T
FIG. 3U
FIG. 3V

FIG. 7A

FIG. 7I $Q_F$ 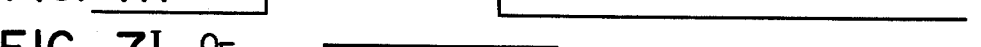
FIG. 7J $Q_G$ 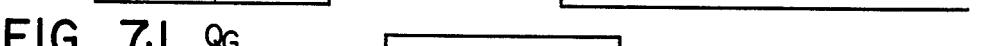
FIG. 7K $Q_H$ 
FIG. 7L $Q_I$ 
FIG. 7M $Q_J$ 
FIG. 7N $Q_K$ 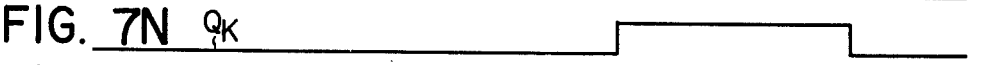
FIG. 7P $Q_L$ 
FIG. 7Q $Q_A$ 
FIG. 7R $Q_B$ 
FIG. 7S $Q_C$ 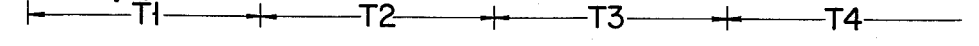
FIG. 7T
|—T1—|—T2—|—T3—|—T4—|

ULTRASONIC WAVE TRANSMITTING AND RECEIVING APPARATUS

This invention realtes to an ultrasonic wave transmitting and receiving apparatus for detecting the shape, structure etc. of a to-be-measured subject utilizing an ultrasonic wave.

An ultrasonic wave transmitting and receiving apparatus is known which is adapted to measure the shape, structure etc. of a subject from an ultrasonic wave radiated in the form of pulses into the subject and reflected in the form of pulses from these portions of the subject which are different in their sound inpedance. The inner structure of the subject can be observed as a whole using such an ultrasonic wave transmitting and receiving apparatus.

A variety of ultrasonic wave transmitting and receiving apparatus have been proposed having a scanning function for use in an ultrasonic tomography. There has recently been developed an ultrasonic wave transmitting and receiving apparatus adapted to either sequentially operate a plurality of electrical-acoustic converting element in the same plane using electronic switches, or effecting a high speed scanning in a plane with a beam of ultrasonic wave through a phase control. By either sequentially energizing through electronic switches the electrical-acoustic elements at high speed for signal transmission and reception or effecting the high-speed phase control of transmitting and receiving pulses from the electrical-acoustic convering elements, a high-speed scanning is performed, making it possible to display the inner structure of the subject substantially at a real time. In practice, several attempts have been made to provide a real time display. This invention is directed particularly to the observation of the interior of a living body. The ultrasonic speed is about 1500 m/s in the living body, i.e., relatively slow and, therefore, a relatively long time is required until the reflected beams are returned from that deep portion of the living body where observation is to be made. For a real time display a predetermined relation will be established between the field of vision, the density of scanning lines and the number of frames. Now consider a rectangular cross-sectional image with N representing the number of frames per second and P the pitch of scanning lines. Then, the area of the field of vision, S, will be $$S < c \cdot P/2N$$

where c denotes the ultrasonic speed in the living body (c $\neq$ 1500 m/s). With S = 200 cm$^2$ and N = 30 frames/s, for example, p > 0.8 mm and the scanning lines will be made coarse.

It is accordingly the object of this invention to provide an ultrasonic wave transmitting and receiving apparatus capable of converting signals received through electrical-acoustic converting elements into signals compressed on a time base and displaying with high-density scanning lines on a display surface the inner structure, shape etc. of a subject to be measured.

According to one embodiment of this invention there is provided an ultrasonic wave transmitting and receiving apparatus comprising a plurality of electrical-acoustic converting elements arranged in a predetermined pattern of array, means for energizing the electrical-acoustic converting elements to generate an ultrasonic wave signal, a plurality of memory circuits adapted to store electric signals corresponding to ultrasonic wave signals reflected from a to-be-measured subject and received through the electrical-acoustic converting elements, and a control circuit adapted to sequentially write the electrical signals at a predetermined rate into the memory circuits and, when any one of the memory circuits is being written, read a memory content from the remaining memory circuits at a rate higher than the predetermined rate.

This invention can be more fully understood from the following detailed description when taken in conjunction with the accompanying drawings, in which:

FIGS. 3A to 3R and 3V show waveform diagrams of a signal at each point of the circuits in FIGS. 1 and 2;

Figure 2:
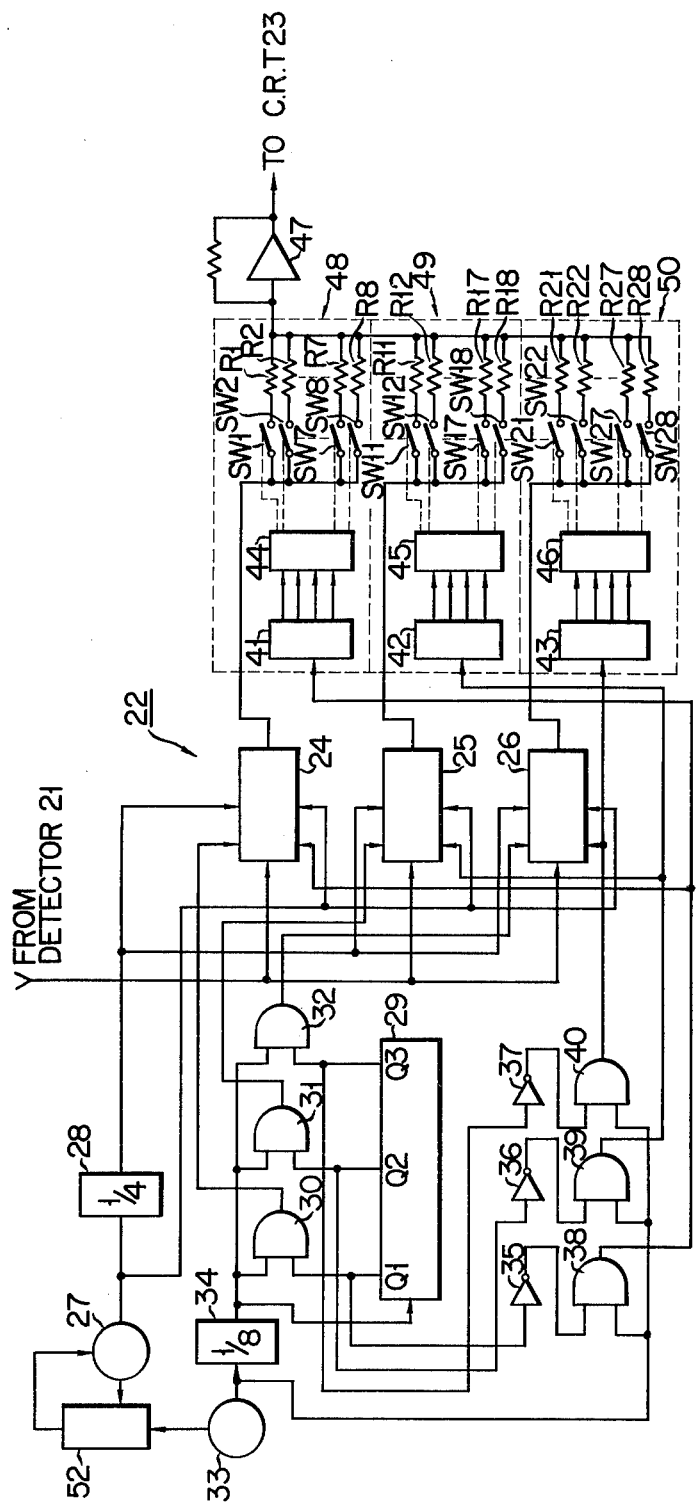
FIG. 2 is a circuit diagram for a signal processing circuit of the ultrasonic wave device in FIG. 1.
Figure 4:
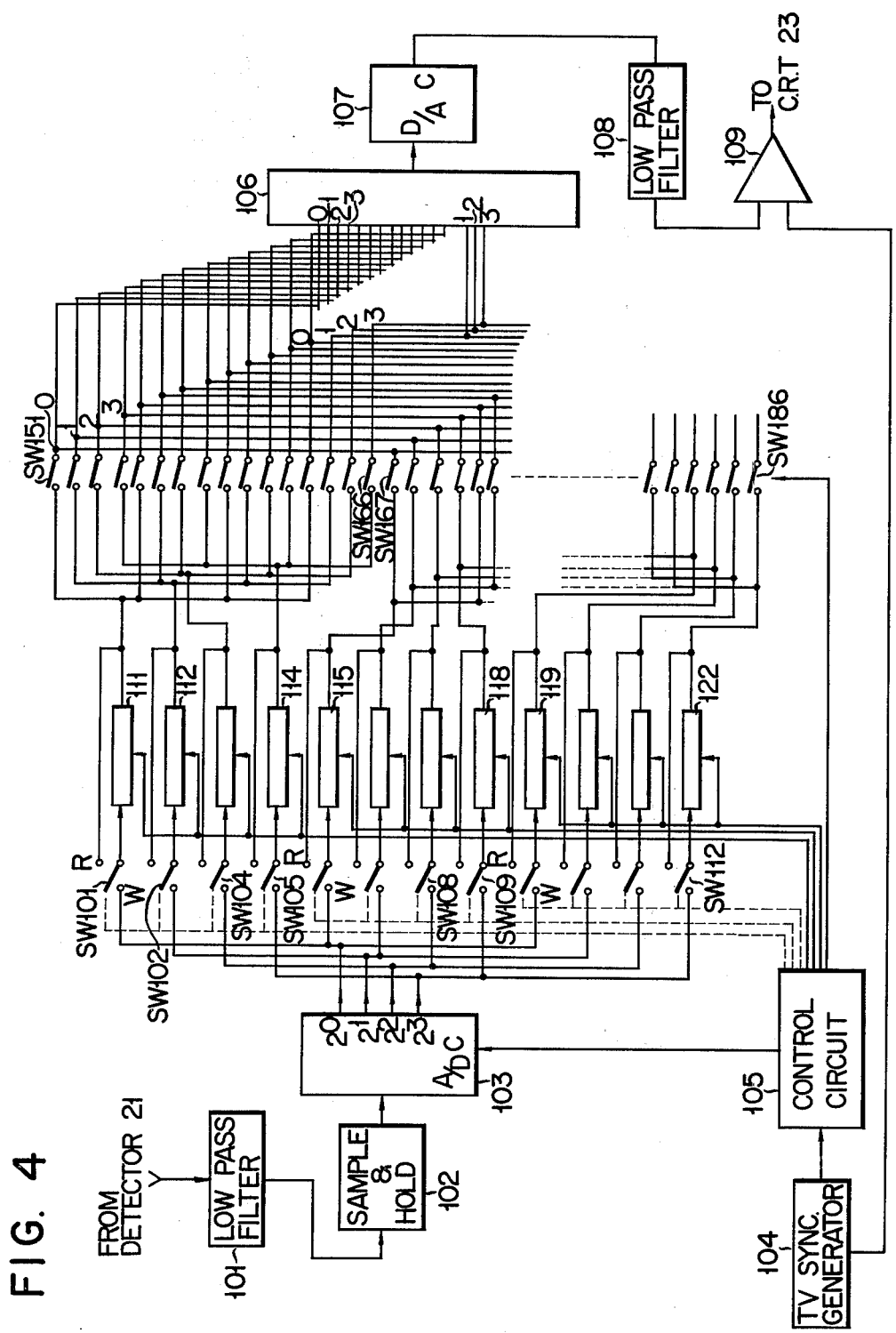
Figure 5:
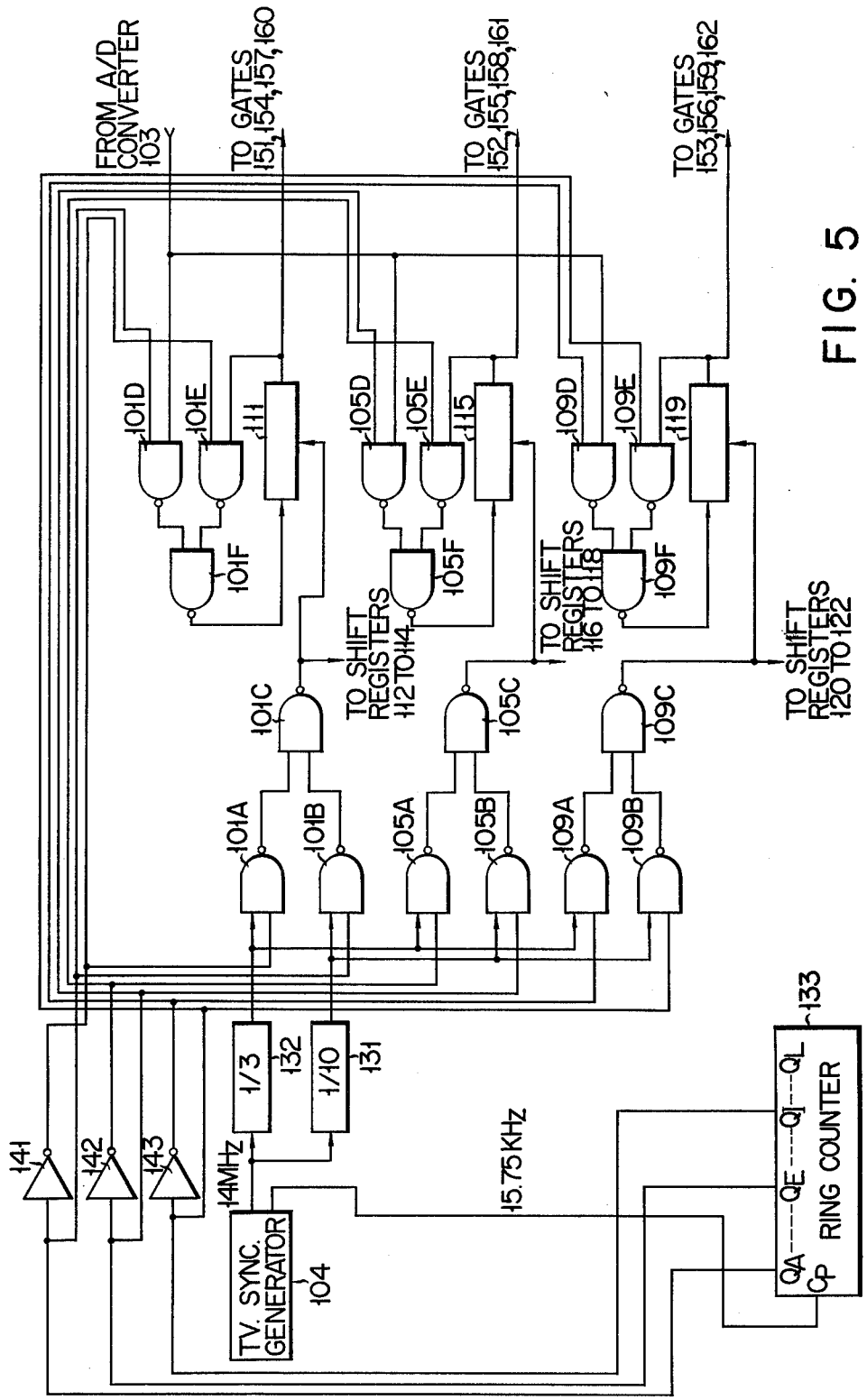
Figure 6:
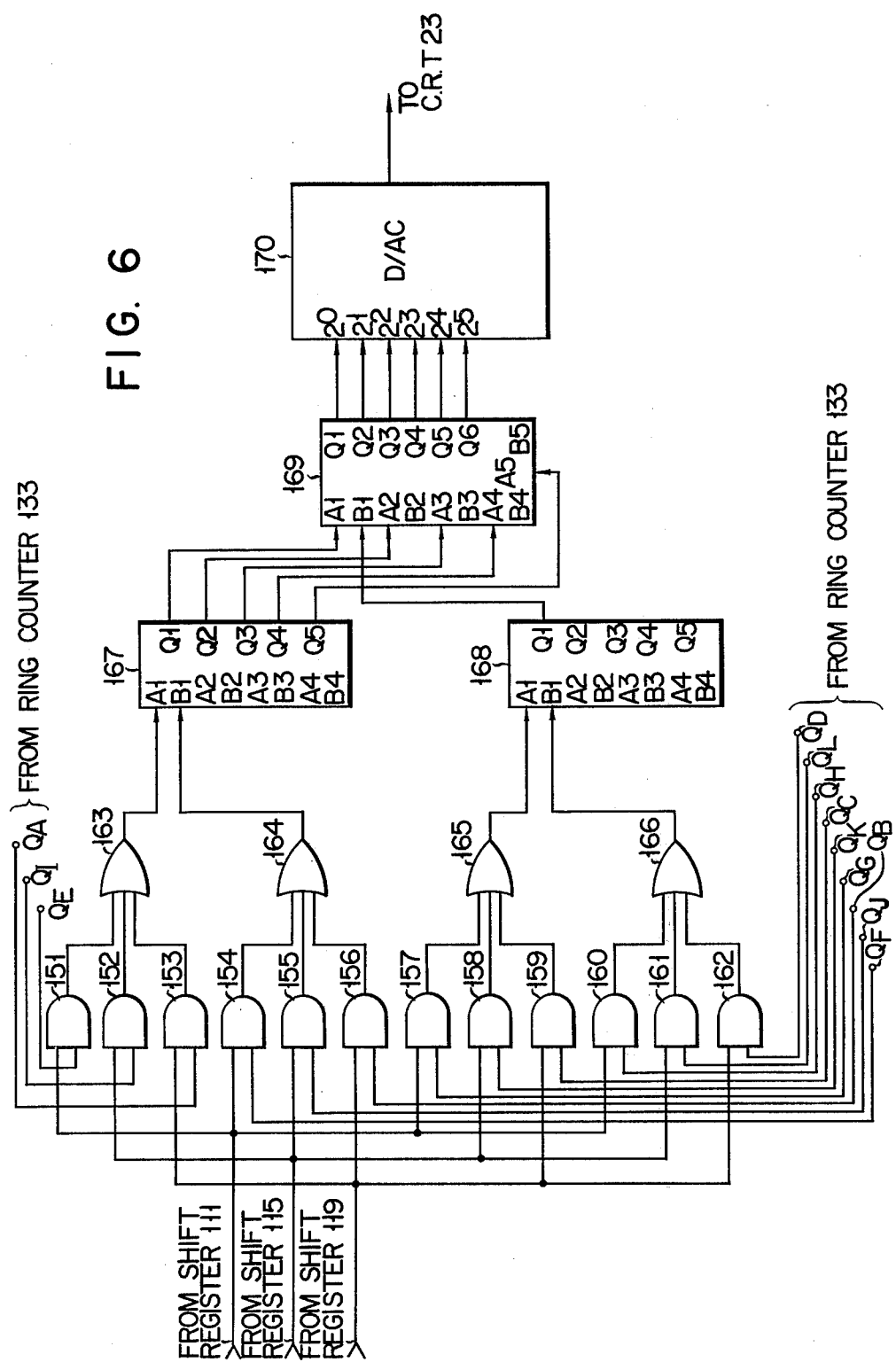
Figure 7B:
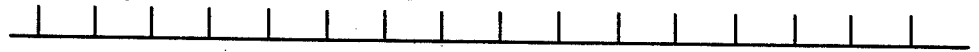
Figure 8:
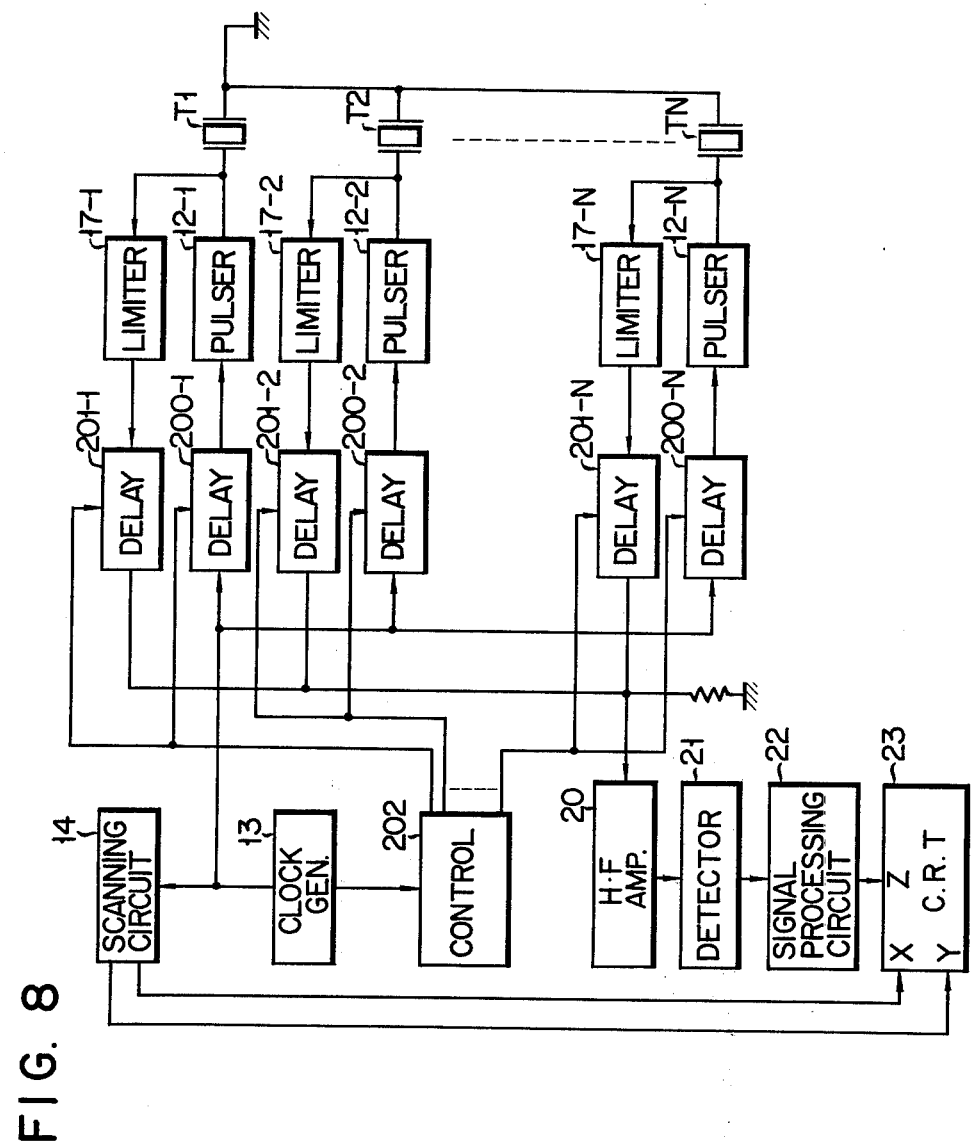

FIGS. 3S to 3U each are a view for explaining the function of a weight setting device for use in the signal processing circuit in FIG. 2;

FIG. 4 is a circuit diagram showing a signal processing circuit of an ultrasonic wave transmitting and receiving apparatus according to another embodiment of this invention;

FIGS. 5 and 6 show a time compression circuit and weight setting circuit for use in a signal processing circuit in FIG. 4;

FIGS. 7A to 7T show a time chart for explaining the operation of the signal processing circuit in FIG. 4; and FIG. 8 is a circuit diagram showing an ultrasonic wave transmitting and receiving apparatus according to another embodiment of this invention in which a sector scanning system is adopted.

An ultrasonic wave transmitting and receiving apparatus according to one embodiment of this invention will be described below by referring to the accompanying drawings.

Figure 1:
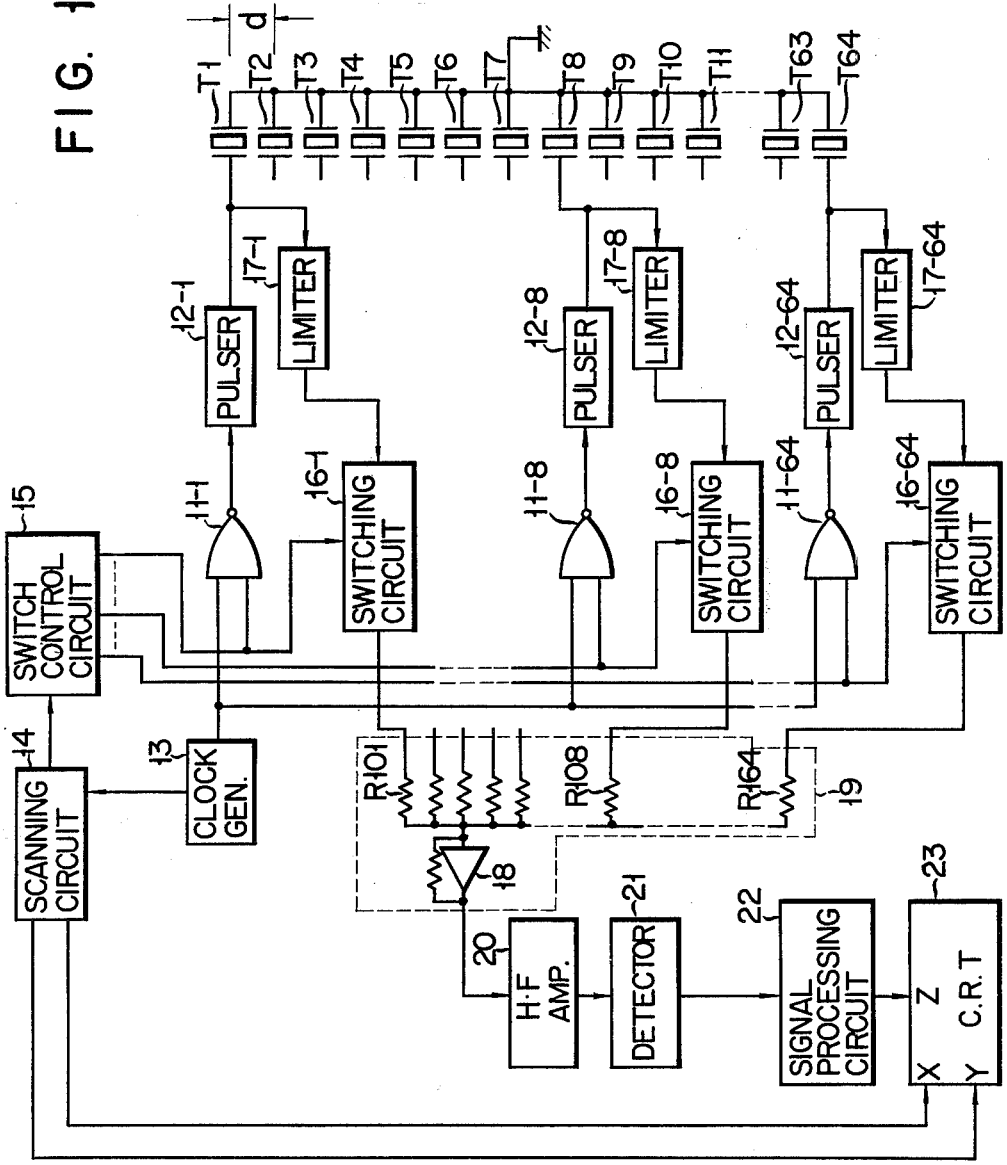
FIG. 1 is an ultrasonic wave transmitting and receiving apparatus according to one embodiment of this invention.

FIG. 1 show an ultrasonic wave transmitting and receiving apparatus according to one embodiment of this invention. The apparatus includes 64 electrical-acoustic converting elemnts T1 to T64 arranged in the same plane with a distance d left therebetween, and a clock pulse generator 13 coupled to NAND gates 11-1 to 11-64 which in turn are connected respectively through pulsers 12-1 to 12-64 to the electrical-acoustic converting elements T1 to T64. The clock pulse generator 13 is coupled to a scanning circuit 14 which in turn is coupled to a switch control circuit 15 connected at one terminal to the clock pulse generator 13 and at the other terminal to the NAND gates. The output terminal of the switch control circuit 15 is also connected to switching circuits 16-1 to 16-64. The electrical-acoustic converting elements T1 to T64 are connected respectively through limiters 17-1 to 17-64 and switching circuits 16-1 to 16-64 to an adding circuit 19 comprising an operational amplifier 18 and resistors R101 to R164 connected to the switching circuits 16-1 to 16-64. The limiter prevents an excess input from being supplied from the pulser to the adding circuit 19. The output of the adding circuit 19 is fed through a high frequency amplifier 20 to a detector 21 and the output signal of the detector 21 is supplied to a signal processing circuit 22 where it is subjected to a time-base compression and weighting processing. The weighted signal is applied to a brightness adjustment terminal Z of a display device 23 such as a cathode ray tube. Terminals X and Y of the display device 23 receive corresponding vertical and horizontal signals from the scanning circuit 14.

The signal processing circuit 22 will be described more in detail by referring to FIG. 2.

The output of the detector 21 is coupled to the input terminal of analog memories 24, 25 and 26. A pulse of, for example, 2.52 MHz is fed from a pulse generator 27 to a divide-by-4 frequency divider 28 to produce a 630 kHz output pulse which is supplied as a write-in command signal to the analog memories 24 to 26. The write-in period is set by a first selection circuit comprising a ring counter 29 and AND gates 30, 31 and 32 having first input terminals respectively coupled to output terminals Q1, Q2 and Q3 of the ring counter 29. The pulse generator 33 delivers an output pulse with a frequency the same as that of a horizontal synchronizing signal, for example, in a television receiver, to a divide-by-8 frequency divider 34 where it is divided into about 2 kHz pulses. Each time the so divided pulse is applied to the input of the ring counter 29 and the second terminals of the AND gates 30 to 32, write-in state setting signals as shown in FIGS. 3D to 3F are sequentially applied to the memories 24, 25 and 26 to cause the latter to be in the write-in state, permitting immediately following write-in command signals as shown in FIGS. 3G to 3I to be sequentially spplied to the memories 24, 25 and 26.

With A-1, A-2, A-3 ... representing signals sequentially generated from the detector 21 in response to the output pulses of a pulse generator 13, the signals A-1, A-2 and A-3 are stored in the analog memories 24, 25 and 26 respectively, signals A-4, A-5 and A-6 in the analog memories 24, 25 and 26 respectively, and so on. The number of bits in each analog memory is represented by $$K = 2lfW/c$$

where
l: maximum distance scanned by an ultrasonic wave
c: velocity of an ultrasonic wave tranvelled in a depth direction through a subject
fW: write-in frequency The repetition cycle $T_0$ of the pulse generator 13 is set to more than two times the value of 2l/c. The signal in each analog memory is read out in response to a 2.52 MHz output pulse from the pulse generator 27 and the readout time period is set by a second selection circuit comprising inverters 35, 36 and 37 respectively coupled to the output terminals Q1, Q2 and Q3 of the ring counter 29 and AND gates 38, 39 and 40 whose first input terminals are connected to the respective outputs of the inverters 35, 36 and 37. Each time the 15.75 kHz output pulse of the pulse generator 33 is applied to the second input terminals of the AND gates 38, 39 and 40, readout state setting signals as shown in FIGS. 3J to 3L are sequentially applied to the analog memories 24, 25 and 26 and immediately following signals as shown in FIGS. 3M to 3P are applied to the analog memories 24, 25 and 26. That is, a readout command signal is applied to the analog memory 24 during the time period in which a data signal is written into the memory 25 or 26. Likewise, a readout command signal is applied to the analog memory 25 or 26 during the time period in which a data signal is written into the other memories. Each readout command signal is applied in a circulating manner to the memory 24, 25 or 26 each time the output pulse is generated from the pulse generator 33. The outputs of the AND gates 38, 39 and 40 are coupled to up-down counters 41, 42 and 43, respectively. The output of the up-down counter 41 is connected to an energizing circuit 44 for selectively energizing switches SW1 to SW8 connected to the analog memory 24, the output of the up-down counter 42 to an enrgizing circuit 45 for selectively energizing switches SW11 to SW18 connected to the analog memory 25, and the output of the up-down counter 43 to an energizing circuit 46 for selectively energizing switches SW21 to SW28 connected to the analog memory 26. The switches SW1 to SW8 are serially coupled respectively through resistors R1 to R8 to an operational amplifier 47, the switches SW11 to SW18 respectively through resistors R11 to R18 to the operational amplifier 47, and the switches SW21 to SW28 respectively through resistors R21 to R28 to the operational amplifier 47. A weight setting circuit 48 comprises the up-down counter 41, energizing circuit 44, switches SW1 to SW8 and resistors R1 to R8; a weight setting circuit 49 comprises the up-down counter 42, energizing circuit 45, switches SW11 to SW18 and resistors R11 to R18; and a weight setting circuit 50 comprises the up-down counter 43, energizing circuit 46, switches SW21 to SW28 and resistors R21 to R28. For a suitable weight setting operation resistors in each of the resistor groups R1 to R8, R11 to R18 and R21 to R28 have the different resistance from each other and resistor in one of the resistor groups have the same resistance as corresponding resistors in the other resistor groups. The energizing circuits 44, 45 and 46 sequentially energize, upon receipt of binary signals from the up-down counters 41, 42 and 43, the corresponding switches in each of the switch groups SW1 to SW8, SW11 to SW18 and SW21 to SW28, causing the signals from the analog memories 24, 25 and 26 to be weighted through the corresponding resistors in each of the resistor groups R1 to R8, R11 to R18 and R21 to R28. The output of the operational amplifier is coupled to a display device 23 such as a cathode ray tube.

The outputs of pulse generators 27 and 33 are coupled to a synchronous device 52 and the pulse generator 27 is controlled by the synchronous device 52 to generate a pulse in synchronism with an output pulse from the pulse generator 33.

The operation of the ultrasonic wave transmitting and receiving apparatus will be explained below.

The electrical-acoustic converting elements T1 to T64 are so operated that upon arrival of a first pulse the elements T1 to T8 are simultaneously energized, upon arrival of a next pulse the elements T2 to T9 are simultaneously energized, upon arrival of a next subsequent pulse the elements T3 to T10 are simultaneously energized, and so on.

For measuring operation the clock pulse 13 is first driven to cause the scanning circuit 14 to be energized to permit an output signal to be delivered to the switch control circuit 15, causing the switch circuit 15 to be driven. The output of the switch control circuit 15 is supplied, for example, to one terminal of the NAND gates 11-1 to 11-8 and the output of the clock pulse generator 13 is coupled to the other terminal of the NAND gates 11-1 to 11-8. The first clock pulse is supplied respectively through the NAND gates 11-1 to 11-8 and pulsers 12-1 to 12-8 to the electrical-acoustic converting elements T1 to T8, permitting a beam of ultrasonic wave to be radiated from the electrical-acoustic converting elements T1 to T8 toward a subject to be measured. The beam reflected on the outer and inner surfaces of the subject is converted through the electrical-acoustic converting elements T1 to T8 to electric signals and, since the switching circuits 16-1 to 16-8 are rendered conductive by the switching control circuits 15, the electric signals are coupled respectively through the limiters 17-1 to 17-8 and switching circuits 16-1 to 16-8 to the adding circuit 19 to generate an output. The output of the adding circuit 19 is supplied through the high frequency amplifier 20 to the detector 21. The detector 21 generates a signal as shown in FIG. 3B and, as mentioned above, the signal components A-1, A-2 ... are sequentially stored at the rate of 630 kHz and, under the control of output signals (see FIGS. 3G and 3I) from the frequency divider 28 and AND gates 30 to 32, into the respective memories 24, 25 and 26. As shown in FIGS. 3Q and 3R, the contents of the memories 24, 25 and 26 are read out at the rate of 2.52 MHz and under the control of output signals (see FIGS. 3M to 3P) from the pulse generator 27 and AND gates 38, 39 and 40. The readout signals of the memories 24, 25 and 26 are given respective weights at the weight setting circuits 48, 49 and 50. In this embodiments, the readout perios is divided into 16 equal sections and weights "0", "1", "2", "3", "4", "5", "6", "7", "8", "7", "6", "5", "4", "3", "2", "1" are sequentially given in this order to corresponding pulses of the readout signals of the respective analog memories 24, 25 and 26. Two of the signals weighted at the weight setting circuits 48, 49 and 50 are overlappingly supplied to the operational amplifier 47 where it generates an output signal as shown in FIG. 3V. In this way, the electrical-acoustic converting elements are energized by the pulses of the clock pulse gnerator 13 and the similar operation is repeated.

In the above-mentioned embodiment, signals are written at the rate of 630 kHz into the memories 24, 25 and 26 and read at the rate of 2.52 MHz out of the memories 24, 25 and 26. In the first period of time T1 in FIG. 3A, for example, a signal A-1 from the amplifier 23 is written at the rate of 630 kHz into the memory 24, and the content A-1 of the memory 24 is read at the rate of 2.52 MHz out of the memory 24 according to the readout pulse during the following period of time 2T1, that is, while signals A-2 and A-3 (FIG. 3A) are being written into the memories 17 and 18. The frequency of an output pulse of the pulse generator 13 is generally determined to be about 2 to 4 kHz, taking into consideration a time required for the radiating ultrasonic wave to be returned from the subject. For this reason, the signal received at the electrical-acoustic converting element can not be used as a CRT (cathode ray tube) video signal with a horizontal syncrhonizing signal of 15.75 kHz. As explained in connection with the above-mentioned embodiment, the received signals are written into the analog memories and the contents of the analog memories are read, at a frequency higher than the write-in frequency, out of the analog memories. By so doing an output signal can be obtained which can be used as video signal for a cathode ray tube. Suppose that the output pulse of the pulse generator 13 has a frequency of, for example, about 2 kHz. In this case it is necessary that in order to obtain a vide signal for the CRT the time base can be compressed by a factor of 8. In this invention, the time base is compressed by a factor of 4 and the half front section of the so compressed, and received data signal is sequentially read out twice and in this sense the result is the same as in the case where the time base is originally compressed by a factor of 8.

In this invention, the frequency, 2 kHz, of an input signal is made four times the original frequency and only the front half section of each signal, i.e., only a true signal A is read out in synchronism with a 15.75 kHz pulse from the pulse generator 13. In consequence, one scan period is equivalently compressed to one-eighth time length and the compressed signal is converted, as shown in FIG. 3Q, to a signal which is synchronized with a horizontal synchornizing signal (15.75 kHz) for the CRT.

Such signals can be used as CRT video signals, but an unnatural picture image is displayed due to some of scanning lines on the CRT being based on the same signals. In order to avoid such an inconvenience the readout period time for each analog memory is made two-times the write-in period of time for each analog memory and every two readout period of time are set overlap each other. The readout signals are coupled to the weight setting circuits 48, 49 and 50 and two signals read out during the same readout time period are added together. The added signal is sent to the operational amplifier 47 to permit an image faithful to a real image to be displayed on the CRT.

For convenience in explanation the received signals are shown in the form of rectangular waves. In practice, however, received signals are composed of a train of pulses with sufficiently short time widths.

In the above-mentioned embodiment the compression ratio of the time base is determined by a ratio between the frequencies of the readout command signal and the write-in command signal and a ratio between the number of scanning lines on the CRT and the number of lines actually scanned is determined by a ratio in frequency between the readout command signal and the write-in command signal. Suppose, for example, that with 60 scanning lines the frequency of the readout command signal is made eight times that of the write command signal. In this case, 480 lines are actually scanned on the CRT.

Although a display on a CRT monitor has been explained by way of example, this invention can also be applied to an ordinary display device by properly selecting a compression ratio and scanning speed. In this embodiment, among all the electrical-acoustic converting elements, M number of elements are simultaneously and linearly scanned stepwise each time the radiated beam of ultrasonic wave is reflected from the subject. It is also possible to effect a sector scanning under the phase control of the electrical-acoustic converting element. The time compression circuit and weight setting circuit can be also applied to, for example, a sector type ultrasonic wave transmitting and receiving apparatus (FIG. 7) for the smoothness of a display signal.

A signal processing circuit in an ultrasonic wave transmitting and receiving apparatus according to another embodiment of this invention will be explained below by referring to FIGS. 4 to 7.

FIG. 4 shows a signal processing circuit. A signal from the detector 21 in FIG. 1 is sent to a low pass filter 101 with an interruption frequency of 700 kHz, where a high harmonic wave and noise are eliminated. The signal is fed through a sample-and-hold circuit 102 to an analog/digital converter 103. The signal of the sample-and-hold circuit 102 is converted at the analog/digital converter 103 to a 4-bit digital signal in response to a write-in control clock pulse from a control circuit 105 adapted to receive an output signal of a synchronizing signal generator 104 in a television receiver. The analog/digital converter 103 has binary terminals $2^0$, $2^1$, $2^2$ and $2^3$ from which corresponding binary output signals are generated. The digital output signal of the analog/digital converter 103 is supplied to shift registers 111 to 114, 115 to 118 or 119 to 122, respectively through electronic switches SW101 to SW104, SW105 to SW108 or SW109 to SW112 which are positioned, by the control circuit 105, on the side of each contact W. The pulse repetition rate of the sample-and-hold circuit 102 and analog/digital converting device 103 and the write-in clock pulse frequency of the shift registers 111 to 122 (for example, 256-bit dynamic shift register) are set to be 1.4 MHz. When, for example, a signal of 256 bits is stored in the shift registers 111 to 114, the switches SW101 to SW104 is closed on the side of each corresponding contact R, causing signals from the analog/digital converter 103 to be read out of the shift registers 111 to 114. When, the switches SW105 to SW108 are positioned on the side of each corresponding contact W to permit signals from the analog/digital converter to be written into the shift registers 115 to 118. The switches SW109 to SW112 are held on the side of the contact R to permit signals from the analog/digital signals to be read out of the shift registers 119 to 122. At this time, the read out clock pulse frequency of the shift register is increased by an amount corresponding to a time compression rate. Where a signal is compressed on a time base by a factor of, for example, 3.3, a readout is effected by a clock pulse frequency of 4.7 MHz. Since also in this embodiment it is necessary to read out the same signal eight times during the readout time, the output signals of the shift registers 111 to 122 are fed through each contact R of the switches SW101 to SW112 back to the input terminal of the shift registers 111 to 122 and it is again written in each of the shift registers 111 to 122. That is, once written signals are read out any number of times until the switches SW101 to SW112 are closed on the side of corresponding contacts W. The shift registers 111 to 114, 115 to 118 and 119 to 122 correspond to the analog memories 24, 25 and 26 of the first embodiment, respectively. Like the first embodiment, when either one set of shift registers is subjected to a writing operation, the other two sets of shift registers effect a readout operation. The analog/digital converting circuit 103 causes an analog signal from the detector 21 to be converted to a digital signal of 4 bits. The 4-bit digital signal of the analog/digital convering circuit 103 is sent to the corresponding shift register of each set of shift registers. The digital output signals of the shift registers 111 to 122 are passed through the switches SW151 to SW186, which are controlled by the control circuit 105 as will be later described, and added together in the digital form at the digital adder 106. The added signal of the digital adder 106 is converted at a digital/analog converter 107 to an analog signal and the analog signal of the digital/analog converter 107 is supplied to a low pass filter 108 with an interruption frequency of 2.3 MHz where high harmonic components are eliminated. The signal passing through the low pass filter 108 is added at an operational amplfifier 109 to a TV synchronizing signal for delivery to a TV monitor.

FIG. 5 shows the control circuit and time base compression circuit shown in FIG. 4. All control signals are obtained from a TV synchronizing generator 104. The frequency of the 14 MHz output signal of the TV synchronizing generator 104 is divided by a divide-by-10 frequency divider 131 and the output of the frequency divider 131 is supplied to gates 101B, 105B and 109B for use as a write-in clock pulse for the shift registers 111 to 122. The frequency of the 14 MHz output signal of the TV synchronizing generator 104 is divided by a divide-by-3 frequency divider 132 and the output of the frequency divider 132 is supplied to gates 101A, 105A and 109A for use as a readout clock pulse for the shift registers 111 to 122. The gates 101A and 101B, 105A and 105B, and 109A and 109B are coupled respectively through gates 101C, 105C and 109C to the shift registers 111, 115 and 119. A ring counter 133 is driven by a 15.75 kHz output signal from the signal generator 104, and the write-in and readout control of the shift registers 111 to 114, 115 to 118 and 119 to 122 are executed by signals respectively from gates 101A and 101B, 105A and 105B, and 109A and 109B and signals supplied respectively through inverters 141, 142 and 143 from the ring counter 133. NAND gates 101D, 105D and 109D are adapted to respectively receive $Q_A$, $Q_E$ and $Q_I$ outputs of the ring counter 133 and an output corresponding to a $2^0$ terminal of the analog/digital converter and NAND gates 101E, 105E, and 109E are adapted to respectively receive inverted ones of output signals from the $Q_A$, $Q_E$ and $Q_I$ outputs of the ring counter 133 and output signals from the shift registers 111, 115 and 119. The NAND gates 101D and 101E, 105D and 105E, and 109D and 109E are coupled to NAND gates 101F, 105F and 109F, respectively. An input signal is supplied to the shift registers 111, 115 and 119 upon receipt of output signals from the NAND gates 101F, 105F and 109F.

Figure 7C:
Figure 7D:
Figure 7E:
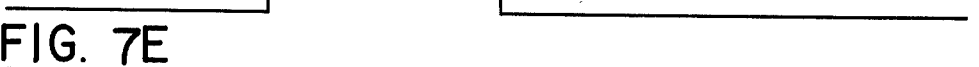
Figure 7F:
Figure 7G:
Figure 7H:

FIGS. 7A to 7F show a time chart relating to the output singal of the ring counter 133. The write-in control signals to the shift registers 111, 115 and 119 are obtained from the $Q_A$, $Q_E$ and $Q_I$ outputs of the ring counter 133. These write-in control signals are as shown in FIGS. 7A, 7C and 7E. The readout control of the shift register 111, 115 and 119 is effected by the $\overline{Q}_A$, $\overline{Q}_E$ and $\overline{Q}_I$ outputs of the ring counter 133 and, as shown in FIGS. 7B, 7D ad 7F, a signal read out, for example, in a period of time T1 is time-compressed in periods of time T2 and T3 by a factor of 4 and read out eight times.

FIG. 6 is one form of the weight setting circuit as shown in FIG. 4. Switches SW151 to SW186 are formed of gates 151 to 162 and OR circuits 163 to 166. These gates 151 to 162 are controlled by output signals from the $Q_A$ to $Q_L$ terminals of the ring counter 133. One example will be explained below. Now consider a ninth clock pulse from the ring counter 133 (see FIG. 7A). At this time, gate open signals are generated from the output terminals $Q_F$ to $Q_I$ and only input signals to the gates 154, 157, 160 and 152 appear from the OR gates 163 to 166. That is, the output of the shift register 115 is coupled to the gate 163 and the outputs of the shift register 111 is coupled to the gates 164, 165 and 166. The outputs of the OR gates 163 and 164 are applied to a digital adder 167 and the outputs of the OR gates 165 and 166 are applied to a digital adder 168. The outputs of these adders 167 and 168 are added at a similar adder 169 and the output signals of the adder 169 are fed to a digital/analog converter 170. In the above-mentioned period of time, therefore, the signal of the shift register 111 and the signal of the shift register 115 are added at a ratio of 3:1. With 10th, 11th and 12th clock pulses from the ring counter, the output signal of the shift register 111 and output signal of the shift register 115 are added at the ratio of 2:2, 1:3 and 0:4, respectively. Since in this case the four weight ratios are given to the output signals of these shift registers, it is ncessary that the digital adders 167 to 169 and digital/analog converter 170 process 6-bit signals. The method for giving the weight to the signal in the digital form requires only a single digital/analog converter and involves a lesser degree of error due to the variation of elements, providing a stable operation. However, the digital signal may be converted to the analog signal before giving the weight to the signal.

Although in FIGS. 5 and 6 the signal processing has been explained in connection with the shift registers 111, 115 and 119 for simplicity of drawings, it will be easily understood that a circuit for processing signals inputted and outputted with respect to the other shift registers may be comprised in the same way as in FIGS. 5 and 6.

FIG. 8 shows an ultrasonic wave transmitting and receiving apparatus according to another embodiment in which like reference numerals are employed to designate parts or elements corresponding to those shown in FIG. 1.

A clock pulse from a clock pulse generator 13 is supplied to delay circuits 200-1 to 200-N. A control circuit 202 is driven by the clock pulse generator 13 and the delay circuits 200-1 to 200-N are so controlled by the control circuit 202 as to have predetermined delay times each time the clock pulse generator 13 generates a pulse. That is, when a first pulse is generated from the clock pulse generator 13, the delay circuits 200-1 to 200-N are so set by the control circuit 202 as to have delay times $0, t_1, 2t_1 \ldots, (N-1)t_1$, respectively. The output signals of the delay circuits 200-1 to 200-N are supplied respectively through pulsers 12-1 to 12-N to electrical-acoustic converting elements T1 to TN. In this case, ultrasonic waves from the electrical-acoustic converting elements are generated with delay times as mentioned above and the wave front of the ultrasonic wave makes an angle of $\theta_1$ to a plane in which the electrical-acoustic converting elements are arranged. In this way the ultrasonic waves directed toward the subject are reflected toward the electrical-acoustic converting elements T1 to TN where they are converted to electric signals. The electric signals are supplied through limiters 17-1 to 17-N and delay circuits 201-1 to 201-N to a high frequency amplifier 21. Like the delay circuits 200-1 to 200-N the delay circuits 201-1 to 201-N are controlled by the control circuit 202 to have delay times as in the case of the delay circuits 200-1 to 200-N.

When a second clock pulse is generated from the pulse generator, the delay circuits 200-1 to 200-N are set by the control circuit 202 to have delay times of $0, t_2, 2t_2 \ldots (N-1)t_2$. As a result, ultrasonic waves from the electrical-acoustic elements T1 to TN are so propagated that the wave front make an angle of $\theta_2$ different from the angle $\theta_1$. In this way, each time pulses are generated from the clock pulse generator 13, the delay circuits 200-1 to 200-N are set to have the predetermined delay times and ultrasonic waves are radiated from the electrical-acoustic elements T1 to TN to make a different angle to a plane in which the electrical-acoustic elements T1 to TN are arranged. A scanning operation is thus effected.

Although in the arrangement of FIG. 8 use is made of the delay circuits 200-1 to 200-N for transmission and the delay circuits 201-1 to 201-N for reception, a single delay circuit may be used for each electrical-acoustic converting element. In this case, the single delay circuit is coupled by a suitable switching circuit to a transmission circuit or a reception circuit, thereby performing the same function as that of the delay circuits in FIG. 8.

What we claim is:

1. An ultrasonic wave transmitting and receiving apparatus comprising:
   a plurality of electrical-acoustic converting elements arranged in a predetermined pattern of array,
   energizing means for energizing the electrical-acoustic converting elements to generate ultrasonic wave signals,
   storing means comprising at least three memory sections for storing electric signals corresponding to ultrasonic wave signals reflected from a to-be-measured subject and received by the electrical-acoustic converting elements,
   display means for displaying information corresponding to ultrasonic wave signals received by the electrical-acoustic elements,
   a control circuit for producing a control signal to causee the memory sections to sequentially set in write-in and readout modes, for sequentially supplying a write-in command signal with a predetermined frequency to at least one of the memory sections which is set in the write-in mode to sequentially write an electric signal at a predetermined rate into the memory section and for sequentially supplying a readout command signal with a frequency higher than that of the write-in command signal to the other memory sections to read out the contents of the other memory sections at a rate higher than the predetermined rate, and
   a weight setting circuit for imparting weight to output signals of the memory sections.

2. An ultrasonic wave transmitting and receiving apparatus according to claim 1 in which said electrical-acoustic converting elements are arranged at equal intervals in a line.

3. An ultrasonic wave transmitting and receiving apparatus according to claim 2, in which said electrical-acoustic converting elements are sequentially energized stepwise a plurality of numbers at a time by the energizing means.

4. An ultrasonic wave transmitting and receiving apparatus according to claim 2 in which the energizing means is adapted to supply phase controlled signals to said electrical-acoustic elements to sequentially generate ultrasonic waves with a different angle for sector scanning.

5. An ultrasonic wave transmitting and receiving apparatus according to claim 1, in which said readout command signals have a frequency synchronized with a horizontal synchronizing signal for a television receiver.

6. An ultrasonic wave transmitting and receiving apparatus according to claim 1, in which said memories comprise analog memories.

7. An ultrasonic wave transmitting and receiving apparatus according to claim 1, in which said memory circuits comprise an analog/digital converter for converting electric signals from said electric-acoustic converting elements to digital signals, and digital memories for storing said digital signals from said analog/digital converter.

8. An ultrasonic wave transmitting and receiving apparatus according to claim 7 further comprising a digital/analog converter for converting the output signals of the weight setting circuit into analog signals.

9. An ultrasonic wave transmitting and receiving apparatus according to claim 7 further comprising a digital/analog converter for converting the output signals of the digital memory means to analog signals.

10. An ultrasonic wave transmitting and receiving apparatus according to claim 1 wherein ultrasonic wave information obtained in response to a single emitting pulse is displayed on the display means by the number of scanning lines corresponding to a ratio in frequency between the readout command signal and the write-in command signal.

11. An ultrasonic wave transmitting and receiving apparatus according to claim 1 wherein the weight setting circuit imparts heavy weight to the central portion of the output signals of the memory sections and light weight to the side portions of the output signals of the memory sections.

* * * * *